US008202298B2

(12) United States Patent
Cook et al.

(10) Patent No.: US 8,202,298 B2
(45) Date of Patent: *Jun. 19, 2012

(54) METHOD AND SUTURE-BUTTON CONSTRUCT FOR STABILIZATION OF CRANIAL CRUCIATE LIGAMENT DEFICIENT STIFLE

(75) Inventors: James L. Cook, Columbia, MO (US); David O. Shepard, Naples, FL (US); Anthony Orozco, Woodstock, GA (US)

(73) Assignee: Arthrex, Inc., Naples, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/012,031

(22) Filed: Jan. 24, 2011

(65) Prior Publication Data

US 2011/0118781 A1 May 19, 2011

Related U.S. Application Data

(63) Continuation of application No. 12/010,184, filed on Jan. 22, 2008, now Pat. No. 7,875,057.

(60) Provisional application No. 60/881,182, filed on Jan. 19, 2007.

(51) Int. Cl.
*A61B 17/04* (2006.01)
*A61B 17/84* (2006.01)
*A61F 2/08* (2006.01)

(52) U.S. Cl. ............ 606/232; 606/300; 623/13.12; 128/898

(58) Field of Classification Search ............ 606/232, 606/300; 623/13.11–13.14, 13.19–13.2; 128/898

See application file for complete search history.

(56) References Cited

U.S. PATENT DOCUMENTS

| 4,187,558 | A | 2/1980 | Dahien et al. |
| 4,712,542 | A | 12/1987 | Daniel et al. |
| 4,739,751 | A | 4/1988 | Sapega et al. |
| 4,772,286 | A | 9/1988 | Goble et al. |
| 4,773,910 | A | 9/1988 | Chen et al. |
| 4,792,336 | A | 12/1988 | Hlavacek et al. |
| 4,823,780 | A | 4/1989 | Odensten et al. |
| 5,139,520 | A | 8/1992 | Rosenberg |
| 5,211,647 | A | 5/1993 | Schmieding |
| 5,234,435 | A | 8/1993 | Seagrave, Jr. |
| 5,281,422 | A | 1/1994 | Badylak et al. |
| 5,300,077 | A | 4/1994 | Howell |

(Continued)

*Primary Examiner* — Dianne Dornbusch
(74) *Attorney, Agent, or Firm* — Dickstein Shapiro LLP

(57) ABSTRACT

An apparatus and method for stabilization of a cranial cruciate ligament deficient stifle in canines using a suture-button construct. The method includes the steps of drilling a femoral hole across a distal femur, passing a needle with a pull-through suture strand of a suture-button construct through the femoral hole, and applying a tensile force to the pull-through suture strand and a suture tape or strand of the construct such that a first button of the suture-button construct lies sideways for passage through the femoral hole, advancing the first button through the femoral hole by pulling the pull-through suture strand until the first button exits the femoral hole, drilling a tibial hole and passing the needle with the pull-through suture strand through the tibial hole, applying a tensile force to the pull-through suture strand and the suture tape or strand of the construct such that the first button lies sideways for passage through the tibial hole, flipping the first button to engage the first button against the medial tibial cortex and subsequently cutting and removing the pull-through suture strand, pulling free ends of the suture tape or strand to advance a second button of the suture-button construct and to seat the second button against the femur, and securing the second button against the femur.

2 Claims, 17 Drawing Sheets

U.S. PATENT DOCUMENTS

| | | | |
|---|---|---|---|
| 5,306,301 A * | 4/1994 | Graf et al. | 606/232 |
| RE34,762 E | 10/1994 | Goble et al. | |
| 5,374,269 A | 12/1994 | Rosenberg | |
| 5,391,171 A | 2/1995 | Schmieding | |
| 5,645,588 A | 7/1997 | Graf et al. | |
| 5,713,897 A | 2/1998 | Goble et al. | |
| 5,769,894 A | 6/1998 | Ferragamo | |
| 6,056,752 A | 5/2000 | Roger | |
| 6,099,568 A * | 8/2000 | Simonian et al. | 623/13.11 |
| 6,110,207 A * | 8/2000 | Eichhorn et al. | 623/13.14 |
| 6,193,754 B1 | 2/2001 | Seedhom | |
| 6,203,572 B1 | 3/2001 | Johnson et al. | |
| 6,245,073 B1 * | 6/2001 | Conteduca et al. | 606/232 |
| 6,254,604 B1 * | 7/2001 | Howell | 606/96 |
| 6,273,890 B1 | 8/2001 | Frazier | |
| 6,355,053 B1 | 3/2002 | Li | |
| 6,383,200 B1 | 5/2002 | Wotton | |
| 6,482,210 B1 | 11/2002 | Skiba et al. | |
| 6,533,802 B2 | 3/2003 | Bojarski et al. | |
| 6,716,234 B2 | 4/2004 | Grafton et al. | |
| 6,736,829 B1 | 5/2004 | Li et al. | |
| 6,764,513 B1 | 7/2004 | Dowling | |
| 6,833,005 B1 | 12/2004 | Mantas et al. | |
| 7,235,091 B2 | 6/2007 | Thornes | |
| 7,238,189 B2 | 7/2007 | Schmieding et al. | |
| 7,819,898 B2 | 10/2010 | Stone et al. | |
| 2002/0007182 A1 | 1/2002 | Kim | |
| 2002/0161439 A1 * | 10/2002 | Strobel et al. | 623/13.14 |
| 2002/0173788 A1 | 11/2002 | Bojarski et al. | |
| 2003/0065391 A1 | 4/2003 | Re et al. | |
| 2003/0176919 A1 | 9/2003 | Schmieding | |
| 2004/0073306 A1 | 4/2004 | Eichhorn et al. | |
| 2004/0153153 A1 | 8/2004 | Eison et al. | |
| 2005/0192631 A1 | 9/2005 | Grafton | |
| 2007/0179531 A1 | 8/2007 | Thornes | |
| 2008/0046009 A1 | 2/2008 | Albertorio | |
| 2008/0097430 A1 * | 4/2008 | Bernstein et al. | 606/60 |
| 2010/0152752 A1 * | 6/2010 | Denove et al. | 606/148 |

* cited by examiner

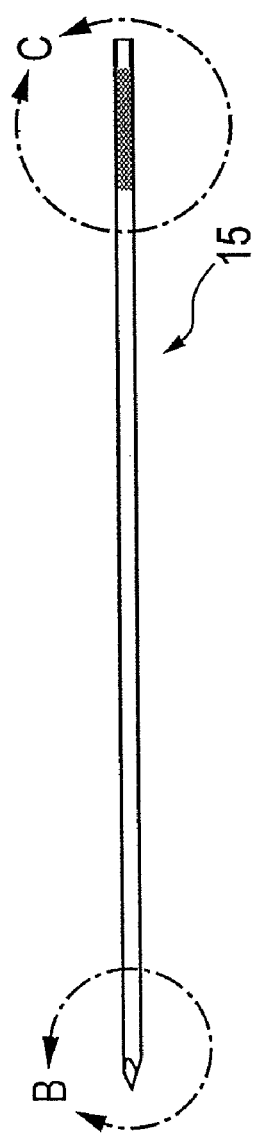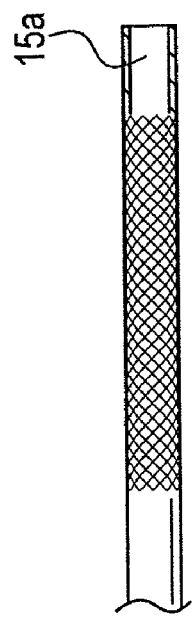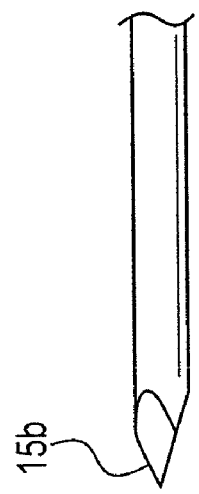
FIG. 7A
FIG. 7C
FIG. 7B

METHOD AND SUTURE-BUTTON CONSTRUCT FOR STABILIZATION OF CRANIAL CRUCIATE LIGAMENT DEFICIENT STIFLE

CROSS REFERENCE TO RELATED APPLICATIONS

This is a continuation of application Ser. No. 12/010,184, filed on Jan. 22, 2008, now U.S. Pat. No. 7,875,057, which claims priority to U.S. Provisional Application No. 60/881,182, filed on Jan. 19, 2007, the entire disclosures of which are hereby incorporated by reference.

BACKGROUND OF THE INVENTION

1. Field of the Invention

The present invention relates to the field of surgery and, in particular, to a method and suture-button construct for stabilization of a cranial cruciate ligament deficient stifle in mammals, in particular, canines.

2. Description of the Related Art

Cranial cruciate ligament (CCL) rupture is the tearing of a ligament in the stifle joint (knee) in canines, resulting in partial or complete joint instability, pain, and lameness. Referring to FIG. 1, the femur 1, tibia 2 and fibula 3 (FIG. 2) meet to form the stifle joint. Ligaments, tendons, and muscles hold the bones in place, stabilize the joint, and enable movement. Articular cartilage attaches to and covers the ends of bones, protecting and cushioning them. A joint capsule, filled with lubricating synovial fluid, surrounds the entire joint.

Referring to FIGS. 1-2, four major ligaments support and stabilize the stifle joint by connecting the femur 1 to the tibia 2 and fibula 3, and the joint capsule to the bones—medial and lateral collateral ligaments 8; caudal and cranial cruciate ligaments 4, 5. The medial and lateral collateral ligaments 8 are located outside the joint. The medial collateral ligament runs from the medial femur 1 to tibia 2. The lateral collateral ligament runs from the lateral femur 1 to head of fibula, passing over the tendon of origin of the popliteus muscle. The medial and lateral collateral ligaments 8 attach to the femur 1 behind the axis of rotation of the femoral condyles and therefore are tensed by extension of the joint.

The caudal and cranial cruciate ligaments 4, 5 are intraarticular ligaments which extend between articular surfaces of femur 1 and tibia 2 and cross one another within the intercondylar notch of the femur. The cranial cruciate ligament 5 attaches to the femur 1, runs across the stifle joint, and attaches to the tibia 2 in a cranial direction (i.e., anterior). The cranial cruciate ligament 5 holds the tibia 2 in place and prevents internal rotation, hyperextension, and cranial translocation of the tibia 2. The caudal cruciate ligament 4 attaches to the femur 1, runs across the stifle joint, and attaches to the tibia 2 in a caudal direction (i.e., posterior). The menisci 6, 7, medial and lateral fibrocartilages located between the femur 1 and the tibia 2, absorbs impact and provides a congruent gliding surface between the femur 1 and tibial 2 plateau.

Cranial cruciate ligament rupture is one of the most common orthopedic injuries in canines and is one of the most common causes of degenerative joint disease in the stifle joint. Chronic or acute rupture of the cranial cruciate ligament consistently results in lameness. Stifle stabilization procedures to address cranial cruciate ligament insufficiency are becoming increasingly important due, at least in part, to increasing pet care awareness.

The goal of treatment is, therefore, to reduce pain and increase mobility of the canine. Multiple surgical procedures—extracapsular imbrication technique, tibial plateau leveling osteotomy and fibular head transposition—are currently available as a form of treatment.

There is a need for an improved surgical procedure for stabilization of a cranial cruciate ligament deficient stifle that is simple, flexible, provides increased strength, and may be performed by a minimally invasive approach, with placement of buttons over the tibia and the femur and secured by a suture-button construct across the stifle joint.

SUMMARY OF THE INVENTION

The present invention fulfills the needs noted above by providing a surgical procedure for stabilization of the cranial cruciate ligament deficient stifle using a suture-button construct in a minimally invasive approach.

The present invention includes a suture-button construct for stabilization of the cranial cruciate ligament deficient stifle formed of a pair of buttons connected by suture strands or a suture tape. In a preferred embodiment of the suture-button construct, the first and second buttons have four apertures each. A strand of suture tape is fed through a first aperture of the second button and through, in turn, opposite apertures of the first button, and through a second aperture of the second button, opposite the first aperture of the second button, to form the suture-button construct, based on intended application. A pull-through suture strand looped through one of the apertures of the first button, other than the apertures through which the suture tape is looped through, is operatively associated with a pull-through needle. The suture tape is preferably a high strength tape formed of ultrahigh molecular weight polyethylene, sold under the brand name FiberTape® by Arthrex, Inc. of Naples, Fla. and disclosed in U.S. Patent Publication No. 2005/0192631, the disclosure of which is herein incorporated by reference. The pull-through suture strand is preferably a high strength suture such as #2 FiberWire® sold by Arthrex, Inc. of Naples, Fla., and disclosed in U.S. Pat. No. 6,716,234, the disclosure of which is incorporated by reference.

In another embodiment of the invention, the first button of the suture-button construct has two apertures while the second button has four apertures, the apertures to allow the passage of suture strands. A first suture strand is fed through a first aperture of the second button and through, in turn, a second and first apertures of the first button and through a second and fourth apertures of the second button and through, in turn, the second and first apertures of the first button and through a third aperture of the second button. A pull-through suture strand is looped through one of the first and second apertures of the first button and is operatively associated with a needle. Preferably, the first suture strand is double looped through the first and second buttons.

The first and second buttons may be formed, for example, of titanium, stainless steel, PolyEtherEther-Ketone (PEEK) or Poly-L Lactic Acid (PLLA). The suture strands may be FiberWire® suture or may be formed of any monofilament or poly-braided material.

The present invention also includes a surgical method for stabilizing the cranial cruciate ligament deficient stifle using a suture-button construct. The method includes providing a suture-button construct as described above. The surgical method should be performed under general or regional anesthesia with appropriate analgesia.

First, the stifle joint is explored via arthrotomy or arthroscopy using a lateral parapatellar approach to complete an exploration of the stifle joint. Pathologic ligament and meniscus are appropriately treated. The joint is thoroughly lavaged and the joint capsule closed to facilitate retraction of the fascia.

After exploratory arthrotomy or arthroscopy, a mini lateral approach to the stifle is performed. An incision is made starting at the level of the lateral fabella to the tubercle of Gerdy and the lateral fascia is incised to allow caudal retraction. A Kirschner wire (also known as "K wire") is inserted immediately cranial and distal to the lateral fabella and within the caudal portion of the lateral femoral condyle. The K wire is advanced at an angle proximally such that the K wire traverses the distal femur and exits the distal diaphysis of the femur on the medial side immediately caudal to the vastus medialis muscle.

A cannulated drill bit is inserted onto the K wire and advanced through the femur to drill a femoral hole. An incision, preferably about 1 cm, is made on the medial aspect of the distal stifle over the drill down to the periosteum to facilitate seating of the first button. The K wire and the drill bit are then removed. A pull-through needle with a pull-through suture strand is passed into the femoral hole from a medial to lateral direction and advanced through the soft tissues on the lateral side.

Lateral tension is applied to the pull-through strand and a simultaneous tension is applied to the suture tape or strand such that a first button of the suture-button construct lies sideways for easy passage through the femoral hole. The first button is advanced through the femoral hole by pulling the pull-through suture strand until the first button exits the femoral hole. The second button is left outside the skin on the medial aspect of the stifle until a tibial hole is drilled and the first button is placed through the tibia.

Next, the long digital extensor tendon (LDE) is palpated within the extensor groove of the proximal lateral tibia. A small incision, preferably about 4-6 mm, is made in the fascia caudal to the long digital extensor tendon. The K wire is placed through this incision and advanced deep to the long digital extensor tendon to rest on tibial bone immediately caudal and/or distal to the tubercle of Gerdy. The K wire is advanced through the proximal tibia at a slight craniodistal angle to exit the tibia on the medial side such that the K wire does not exit the skin on the medial side. A cannulated drill bit is inserted over the K wire and advanced through the tibia to make the tibial hole such that the drill bit does not exit the skin on the medial side. Subsequently, the K wire and the drill bit are removed from the tibia.

Next, the pull-through needle with the pull-through suture strand is advanced through the tibial hole in a lateral to medial direction such that the pull-through needle exits through the skin. Tension is applied to the pull-through suture strand and a simultaneous tension is applied to the suture tape/suture strand such that the first button lies sideways for easy passage through the tibial hole.

Once the first button has exited the tibial hole, the first button is flipped in the subcutaneous space by pulling the pull-through suture strand in a slight upward direction and then by pulling back on the suture tape/suture strand. The first button is then firmly seated against the medial tibial cortex. The pull-through suture strand is then cut and removed. All slack in the suture tape/suture strand is removed by pulling on the suture tape/suture strand at the tibial hole on the lateral side to ensure that the first button is seated firmly. Any remaining slack in the suture tape/suture strand is removed by pulling on the free ends of the suture tape/suture strand near the second button. This can be repeated for a second suture strand when a two-suture construct is used.

Subsequently, the second button is advanced through the soft tissue and is seated against the femoral bone. The suture tape/suture strand is pulled to the desired tension on the medial side of the femur. A surgeon's knot and two half hitches are tied in the suture tape or strand while holding the stifle joint at a desired angle. The stifle joint is then tested for stability and motion. Two or three additional half hitches are then tied. Any excess suture strand is cut away.

Finally, the muscle and fascia over the second button and knot are closed in a routine fashion. The lateral fascia is imbricated and the lateral subcutaneous tissues and the skin are closed in a routine fashion.

The suture-button construct, in accordance to a preferred embodiment of the invention, includes an oblong-shaped button with four circular-shaped apertures. The four apertures are spaced such that there are two rows and columns of two apertures each, the centers of the apertures being spaced equally along a row and a column.

The suture-button construct, in accordance with another embodiment of the present invention, includes a button having an oblong body with first and second apertures, each of the apertures being tapered and terminating in a respective apex, the respective apices being directed away from each other and being located substantially about a longitudinal mid-line of the oblong body. Preferably, each aperture is substantially triangular in plan view. More preferably, each of the apertures has first, second and third sides and the first sides of the respective first and second apertures are substantially parallel. More preferably, the second and third sides of each aperture are of substantially the same length while being longer than the first side.

The first and second apertures of the oblong button can have any shape, provided that each aperture is tapered and terminates in a respective apex. In one preferred embodiment, the aperture is substantially triangular in plan view. In another embodiment, the aperture is an egg-shaped or oval aperture, the curved narrower end comprising the apex.

The suture-button construct also includes a button with a round body having four apertures, each of the apertures being located substantially equidistant from the center of the round body. Preferably, each aperture is substantially round in plan view. In another embodiment, the button is cup-shaped.

The round button may have any suitable dimension (diameter and thickness). For example, the round button may have a diameter of about 5.5 mm and a thickness of about 1.27 mm. The centers of the four apertures are about 1.27 mm from the center of the button and the centers of a first pair of apertures lie substantially along an axis passing through the center of the button. The axis connecting the centers of the remaining two apertures, i.e., a second pair of apertures, is substantially perpendicular to the axis connecting the centers of the first pair of apertures.

The apertures of the round button can have any shape, provided that each aperture is equidistant from the center of the round body. One preferred embodiment is an aperture, which is substantially round in plan view. Another embodiment is an egg-shaped or oval aperture.

These and other features and advantages of the present invention will become apparent from the following description of the invention that is provided in connection with the accompanying drawings and illustrated embodiments of the invention.

BRIEF DESCRIPTION OF THE DRAWINGS

FIG. 7 illustrates a front and plan view of a pull-through needle used in the present invention;

DETAILED DESCRIPTION OF THE PREFERRED EMBODIMENTS

The present invention is a method and apparatus for stifle stabilization for treatment of cranial cruciate ligament deficiency, which utilizes a suture-button construct that is placed over the tibia and the femur.

Figure 1:
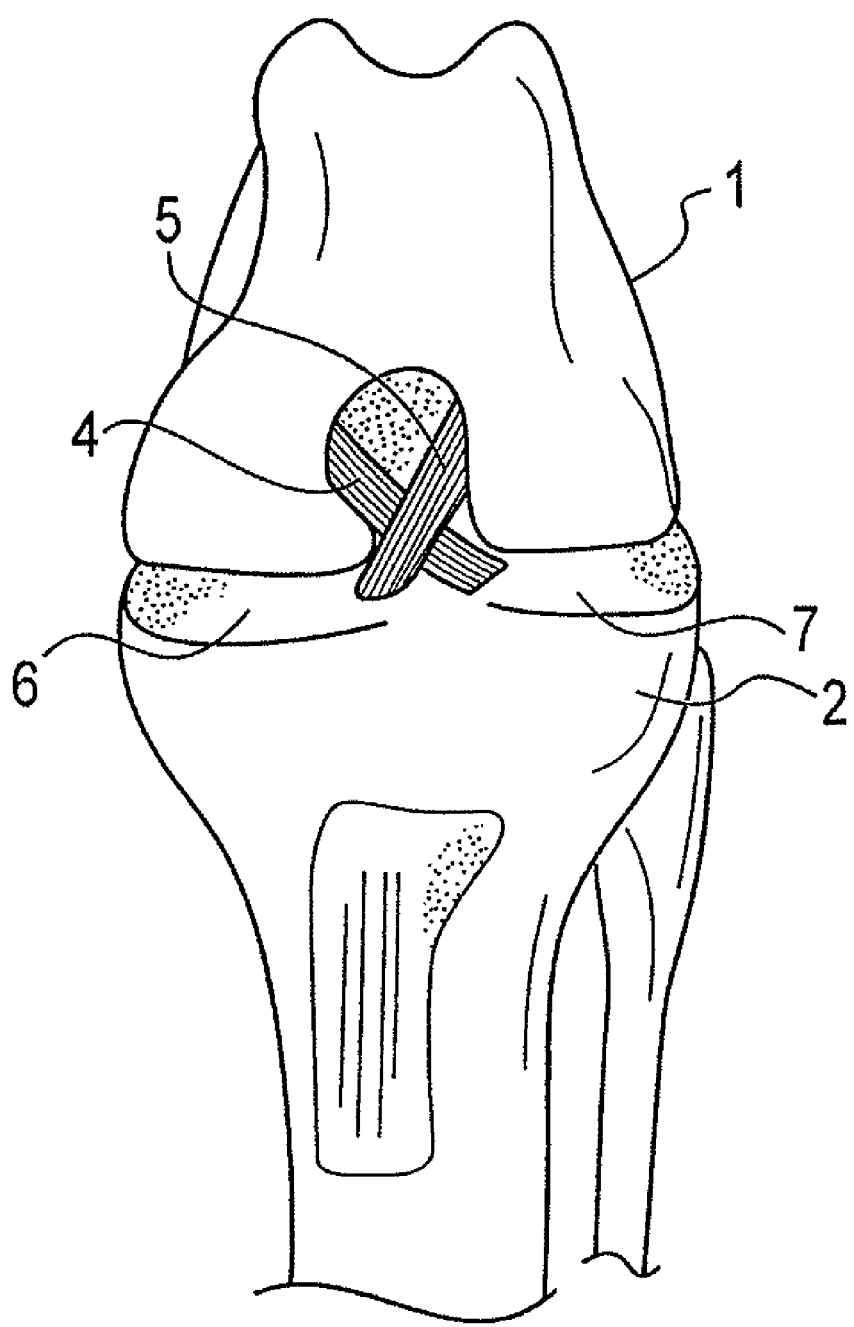
FIG. 1 illustrates the cranial (front) view of a canine stifle joint anatomy.
Figure 2:
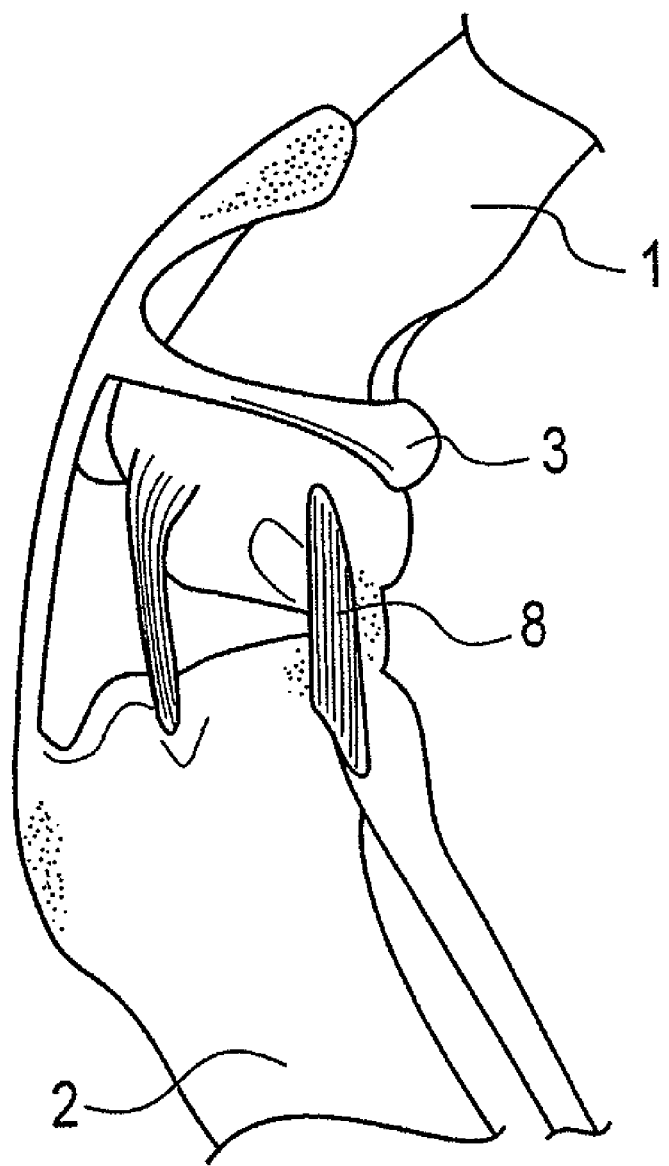
FIG. 2 illustrates the lateral (side) view of a canine stifle joint anatomy.
Figure 3:
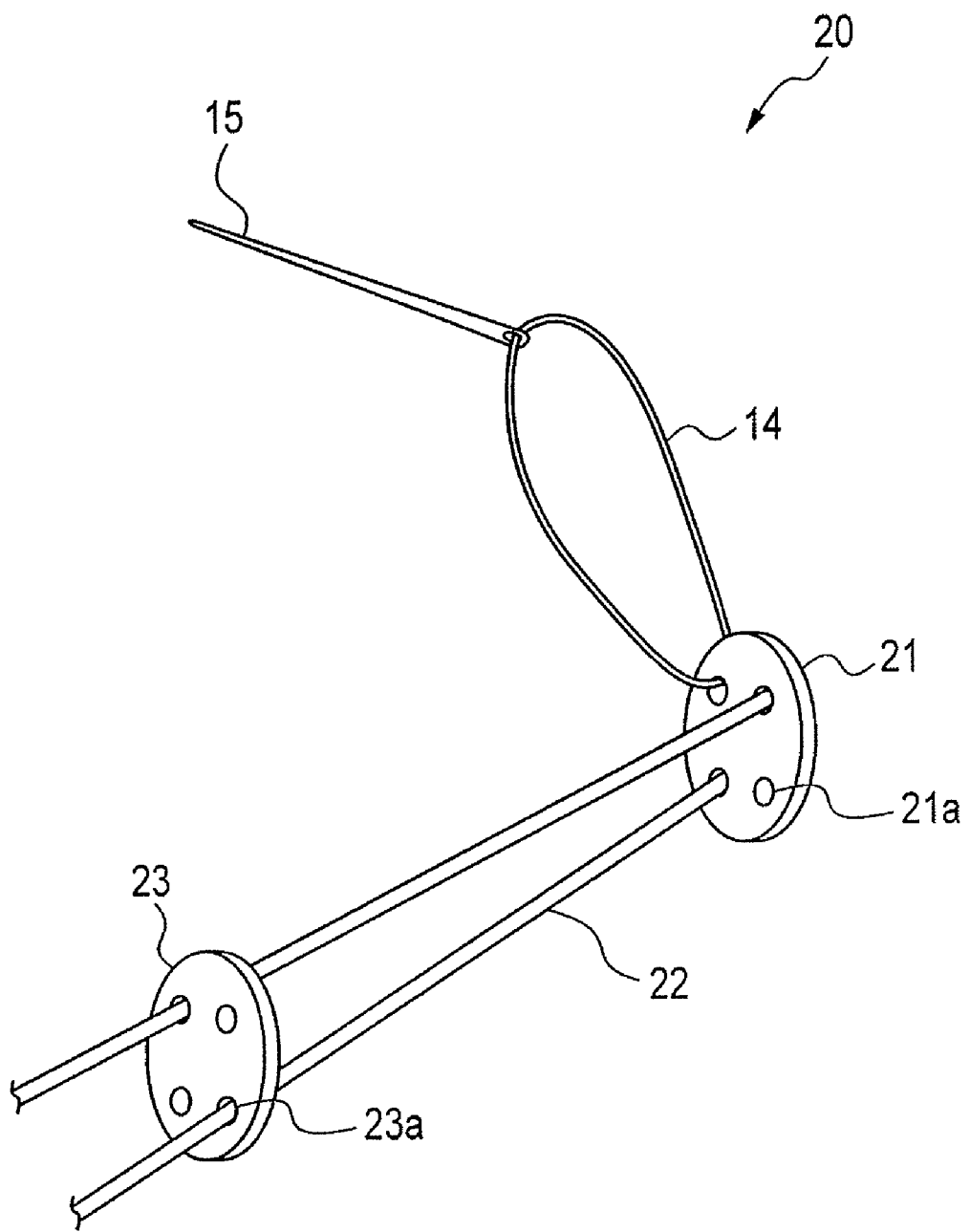
FIG. 3 illustrates a perspective view of assembled suture-button construct, in accordance with a first embodiment of the present invention.
Figure 4A:
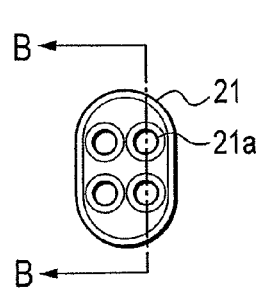
FIG. 4 illustrates a front and side view of an oblong button which forms part of the suture-button construct, in accordance with the first embodiment of the present invention.
Figure 4B:
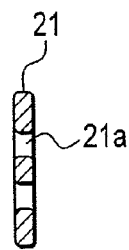

Referring to FIG. 3, a suture-button construct 20, in accordance with a first embodiment of the present invention, is formed of a first button 21, a second button 23, and a suture tape 22. The first and second buttons 21, 23 have four apertures 21a, 23a each. The suture tape 22 is fed through a first aperture of the second button 23 and through, in turn, opposite apertures of the first button 21, and through a second aperture of the second button 23, opposite the first aperture of the second button. The suture-button construct 20 also includes a pull-through needle 15 with a pull-through suture strand 14 looped through an aperture 21a of the first button 21. The first and second buttons 21, 23 are preferably oblong in shape, as shown in FIG. 4.

Figure 5:
FIG. 5 illustrates a front view of a suture tape which forms part of the suture-button construct, in accordance with the first embodiment of the present invention.
Figure 6:
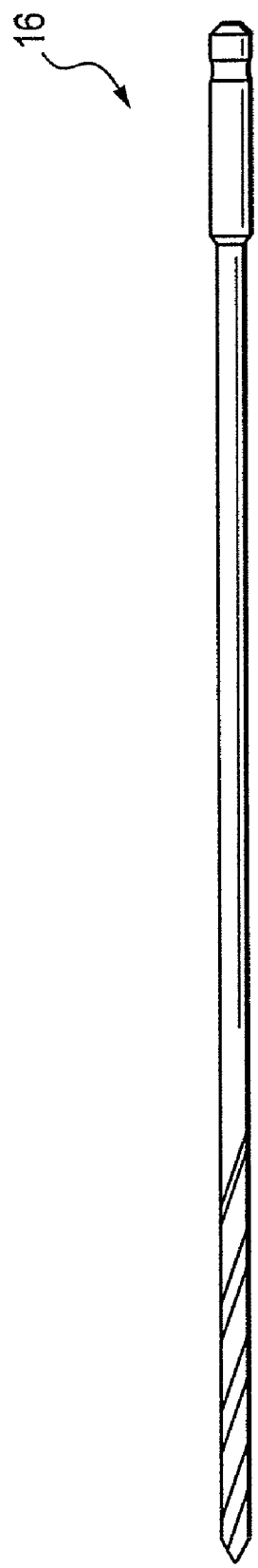
FIG. 6 illustrates a plan view of a cannulated drill bit used in the present invention.

Referring to FIG. 5, the suture tape 22 used in the present invention includes a suture 22a. The preferred suture tape 22 is sold under the brand name FiberTape® by Arthrex, Inc. of Naples, Fla. and disclosed in U.S. Patent Publication No. 2005/0192631, the disclosure of which is herein incorporated by reference.

TABLE 1

Apparatus of the present invention

First and Second Buttons

| | |
|---|---|
| Overall dimensions: | 12.0 mm (length) × 7.5 mm (width) × 1.5 mm (thickness) |
| Basic shape: | Oblong in plan shape, with chamfered or rounded corners and edges - this reduces the chance of the button being palpated under the skin and in addition, eases the passage of the button through the drill hole as will be explained hereinafter |
| Button material: | Titanium, stainless steel, PEEK or PLLA |
| Button apertures: | 4 apertures (circular in plan shape), centers of two of the apertures are at about 4.03 mm along the length and centers of two of the apertures are at about 3.166 mm along the width |
| Aperture dimensions: | 2.0 mm (diameter) (free of burrs or sharp edges) |

Suture tape

| | |
|---|---|
| Dimensions: | 0.54 mm to 0.859 mm (Fibertape ®), 2.25 mm to 4.0 mm (total thickness), 762 mm to 914.4 mm (length) |
| Suture tape material: | Fibertape ® with a #2 FiberWire ® inside (FiberWire ® is made of ultra-high molecular weight polyethylene (UHMWPE) and polyester, braided over a UHMWPE core). |
| Suture tape use: | Looped through opposing apertures of the first button, threading through opposing apertures of the second button, leaving the two free ends of suture tape free for tying. |

TABLE 1-continued

Apparatus of the present invention

| | |
|---|---|
| Suture tape length: | About 4 inches between the first and second buttons |
| Suture tape color: | D&C Blue or White |

Pull-through suture strand

| | |
|---|---|
| Dimensions: | 0.330-0.381 mm (diameter), 0.75 mm (length) |
| Suture material: | #2 FiberWire ®, white in color (FiberWire ® is made of ultra-high molecular weight polyethylene (UHMWPE) and polyester, braided over a UHMWPE core) |
| Suture use: | Looped once through an aperture of the first button, both free ends of pull-through suture strand being attached through the eye of the pull-through needle |
| Suture color: | D&C Blue, White, White/Green |

Pull-through needle

| | |
|---|---|
| Dimensions: | 127 mm (length), 1.6 mm (diameter), with pull-through suture strand attached |
| Material: | Stainless steel |
| Eyelet dimensions: | 0.1 mm (length), 0.965 mm (diameter) |
| Guidewire | 1.2 mm (diameter) |

Cannulated Drill Bit

| | |
|---|---|
| Dimension: | 178 mm (length) × 2.7 mm (diameter), 1.35 mm cannulation for a guidewire to pass through |
| Material: | Stainless steel |

The pull-through suture strand to be used in the apparatus of the present invention may be of any material, which is suitable for this purpose, whether absorbable or non-absorbable, provided it is sufficiently strong. A #2 FiberWire® suture is preferred but a #5 FiberWire® may also be used.

A cannulated drill bit 16, preferably a 2.7 mm drill bit, is used to drill a hole for the suture tape and the pull-through suture strand. The diameter of the hole must be sufficient to permit the first button to be pulled, lengthways, thereto.

Referring to FIG. 7, the pull-through needle 15 has an eyelet 15a on one end and a pointed tip 15b at another end. The pull-through needle 15 may be of any dimensions, provided it is long enough to span the foot. The tip of the pull-through needle can be either "taper cut" or "cutting."

Surgical Technique

The surgical procedure may be performed under general or regional anesthesia with appropriate analgesia. First, the stifle joint is explored via arthroscopy using a lateral parapatellar approach, or via arthroscopy using standard portals, to complete an exploration of the stifle joint. Pathologic ligament and meniscus are appropriately treated. The joint is thoroughly lavaged and the joint capsule closed to facilitate retraction of the fascia.

Figure 8:
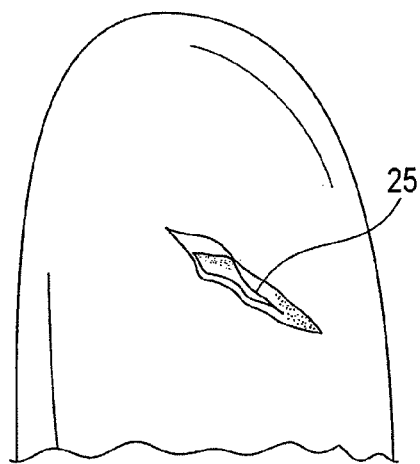
FIG. 8 illustrates a method of stabilization of cranial cruciate ligament deficient stifle according to the present invention and shows a stifle joint at a preparation stage.
Figure 9:
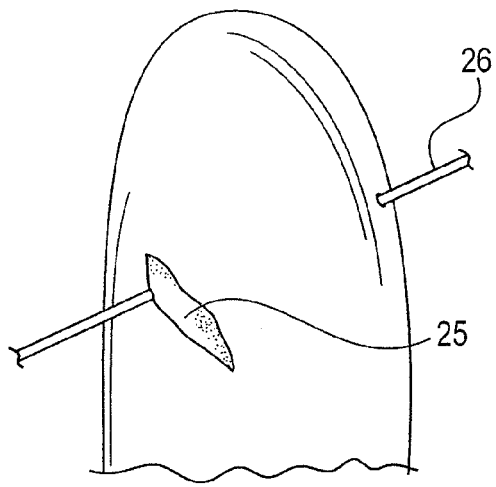
FIG. 9 illustrates the stifle joint of FIG. 8 at a stage subsequent to that shown in FIG. 8 and shows a Kirschner wire placed cranial and distal to the lateral fabella.
Figure 9A:
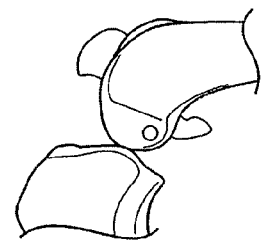
Figure 10:
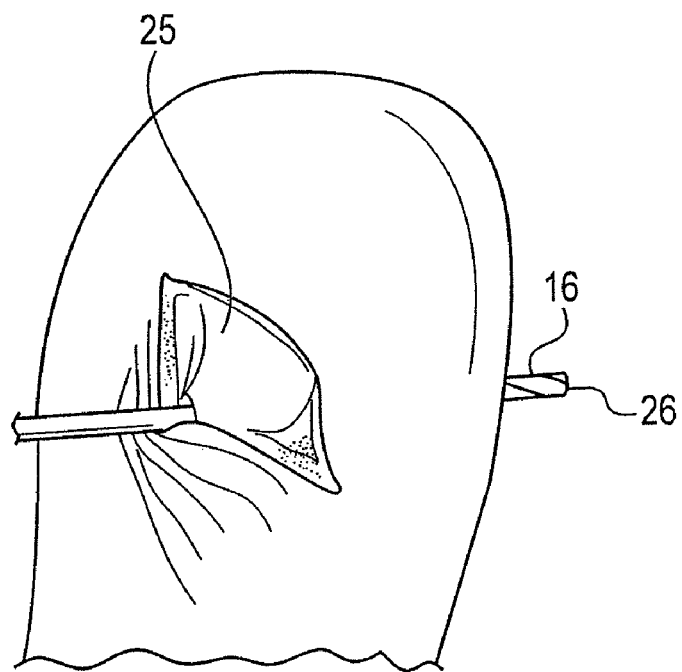
FIG. 10 illustrates the stifle joint of FIG. 8 at a stage, subsequent to that shown in FIG. 9 and shows a drill bit placed immediately proximal to the fabella.

After exploratory arthrotomy or arthroscopy, a mini lateral approach to the stifle is performed. Referring to FIGS. 8-9, an incision 25 is made starting at the level of the lateral fabella to the tubercle of Gerdy and the lateral fascia is incised to allow caudal retraction. A Kirschner wire 26 (also known as "K wire") is inserted immediately cranial and distal to the lateral fabella and within the caudal portion of the lateral femoral condyle. The K wire 26 is advanced at an angle proximally such that the K wire 26 traverses the distal femur and exits the distal diaphysis of the femur on the medial side immediately caudal to the vastus medialis muscle.

Figure 11:
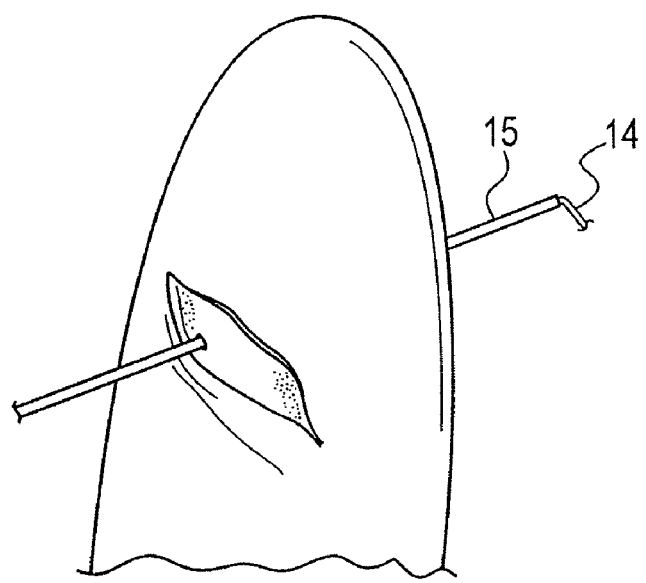
FIG. 11 illustrates the stifle joint of FIG. 8 at a stage subsequent to that shown in FIG. 10 and shows the insertion of a needle with pull-through suture strand.

A cannulated drill bit 16 is inserted onto the K wire 26 and advanced through the femur to drill a femoral hole. An incision, preferably about 1 cm, is made on the medial aspect of the distal stifle over the drill down to the periosteum to facilitate seating of the first button 21 (FIG. 3). The K wire 26 and the drill bit 16 are then removed. Referring to FIG. 11, a pull-through needle 15 with a pull-through suture strand 14 is passed into the femoral hole from medial to lateral direction and advanced through the soft tissues on the lateral side.

Figure 12:
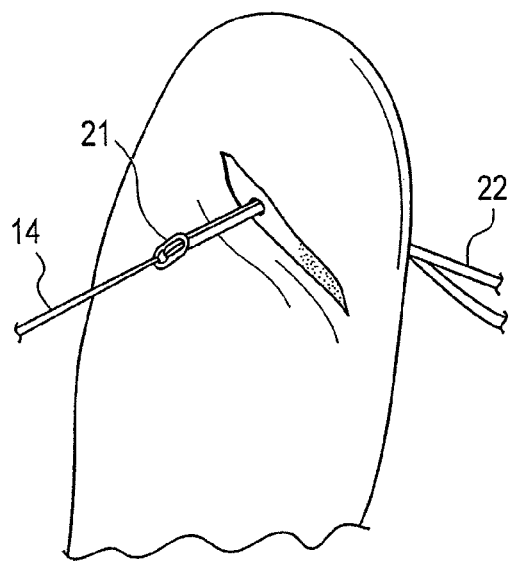
FIG. 12 illustrates the stifle joint of FIG. 8 at a stage subsequent to that shown in FIG. 11 and shows the pull-through suture strand being pulled from a lateral side of the femur.

A lateral tension is applied to the pull-through strand 14 and a simultaneous tension is applied to a suture tape 22 such that the first button 21 of the suture-button construct lies sideways for easy passage through the femoralhole, as shown in FIG. 12. The first button 21 is advanced through the femoral hole by pulling the pull-through suture strand 14 until the first button 21 exits the femoral hole. The second button 23 (FIG. 13) is left outside the skin on the medial aspect of the stifle until a tibial hole is drilled and the first button is placed through the tibia.

Figure 13:
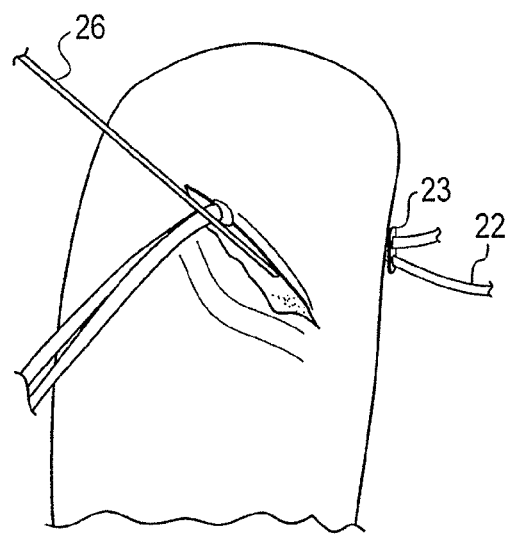
FIG. 13 illustrates the stifle joint of FIG. 8 at a stage subsequent to that shown in FIG. 12 and shows a Kirschner wire placed proximal to the cranial tibial muscle head.
Figure 13A:
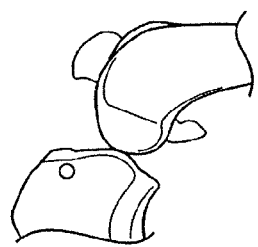
Figure 14:
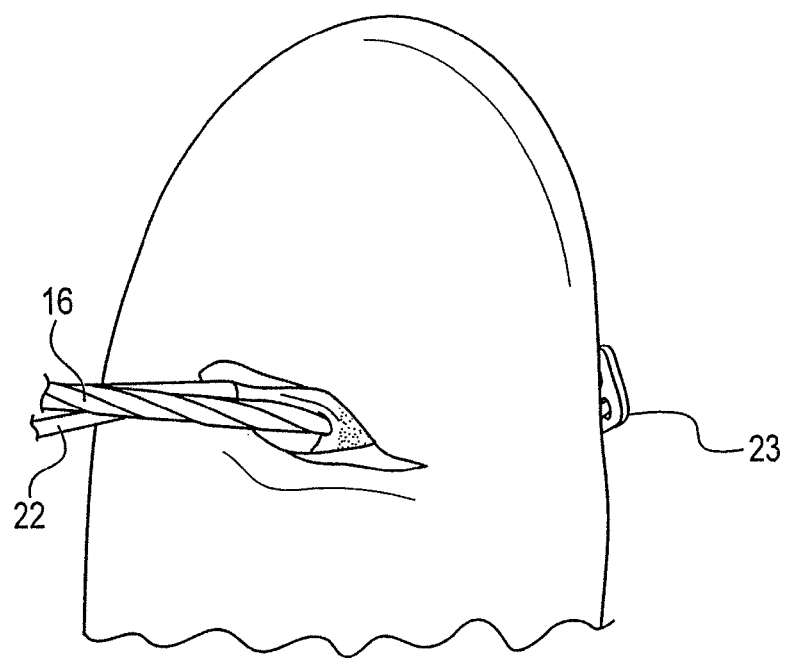
FIG. 14 illustrates the stifle joint of FIG. 8 at a stage subsequent to that shown in FIG. 13 and shows a drill bit placed over the Kirschner wire.

Next, the long digital extensor tendon (LDE) is palpated within the extensor groove of the proximal lateral tibia. A small incision, preferably about 4-6 mm, is made in the fascia caudal to the long digital extensor tendon. As shown in FIG. 13, the K wire 26 is placed through this incision and advanced deep to the long digital extensor tendon to rest on tibial bone immediately caudal and/or distal to the tubercle of Gerdy. The K wire 26 is advanced through the proximal tibia at a slight craniodistal angle to exit the tibia on the medial side such that the K wire 26 does not exit the skin on the medial side. Referring to FIG. 14, a cannulated drill bit 16 is inserted over the K wire 26 and advanced through the tibia to make the tibial hole such that the drill bit 16 does not exit the skin on the medial side. Subsequently, the K wire 26 and the drill bit 16 are removed from the tibia.

Figure 15:
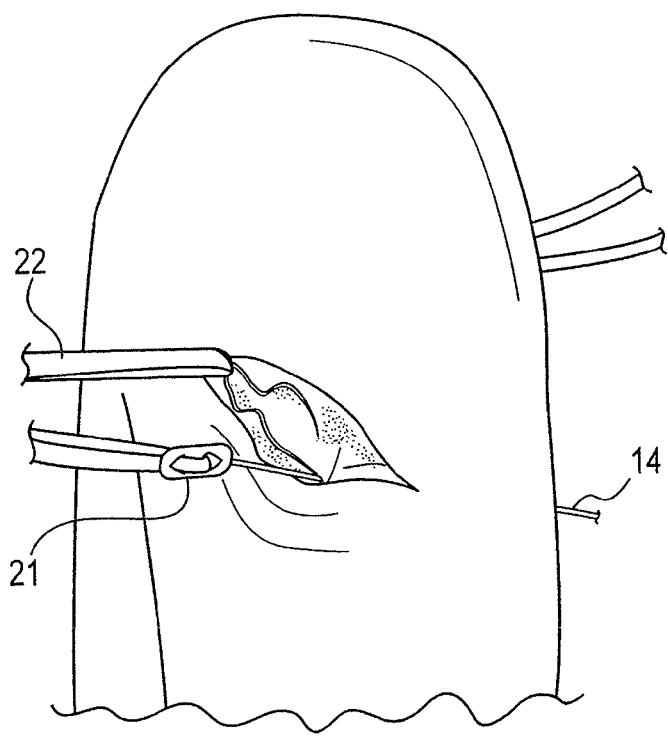
FIG. 15 illustrates the stifle joint of FIG. 8 at a stage subsequent to that shown in FIG. 14 and shows the pull-through suture strand being pulled to advance a first button of the construct through the tibial hole.

Referring to FIG. 15, the pull-through needle 15 (FIG. 11) with the pull-through suture strand 14 is advanced through the tibial hole in a lateral to medial direction such that the pull-through needle 15 (FIG. 11) exits through the skin. Tension is applied to the pull-through suture strand 14 and a simultaneous tension is applied to the suture tape 22 such that the first button 21 lies sideways for easy passage through the tibial hole.

Figure 16:
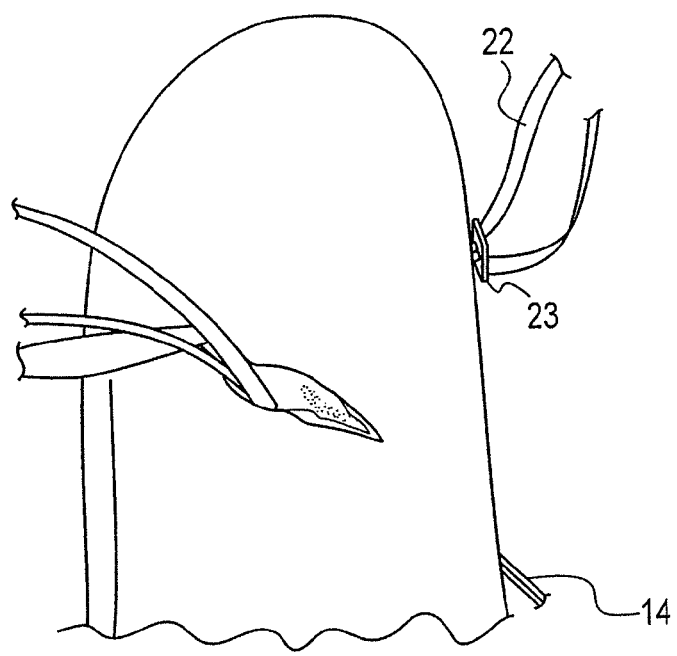
FIG. 16 illustrates the stifle joint of FIG. 8 at a stage subsequent to that shown in FIG. 15.
Figure 17:
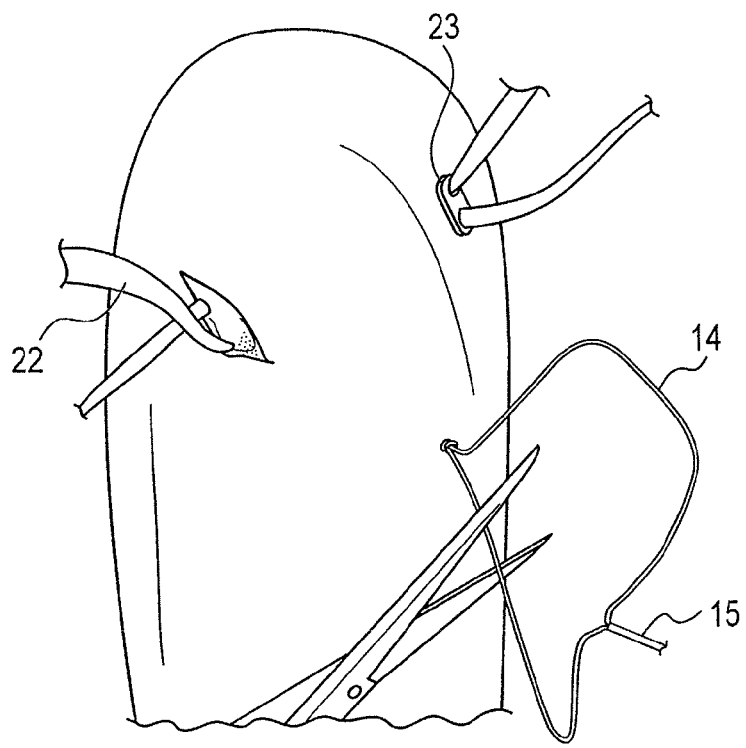
FIG. 17 illustrates the stifle joint of FIG. 8 at a stage subsequent to that shown in FIG. 16 and shows the cutting of the pull-through suture strand of the construct.

Once the first button 21 (FIG. 15) has exited the tibial hole, the first button 21 (FIG. 15) is flipped in the subcutaneous space by pulling the pull-through suture strand 14 in a slight upward direction and then by pulling back on the suture tape 22, as shown in FIG. 16. The first button 21 (FIG. 15) is then firmly seated against the medial tibial cortex. Referring to FIG. 17, the pull-through suture strand 14 is then cut and removed.

Figure 18:
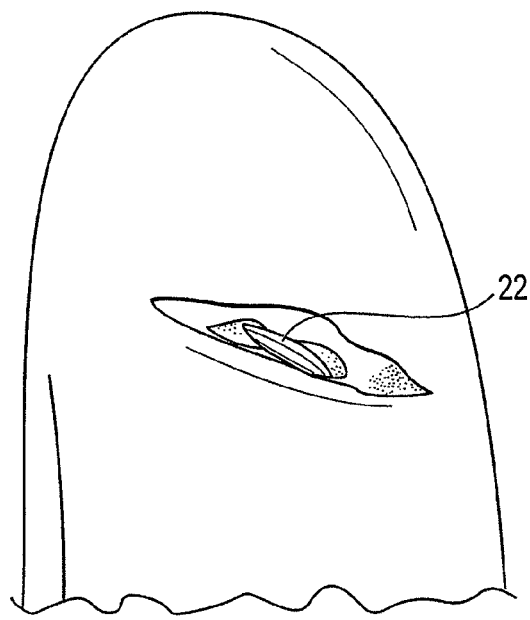
FIG. 18 illustrates the stifle joint of FIG. 8 at a stage subsequent to that shown in FIG. 17.
Figure 19:
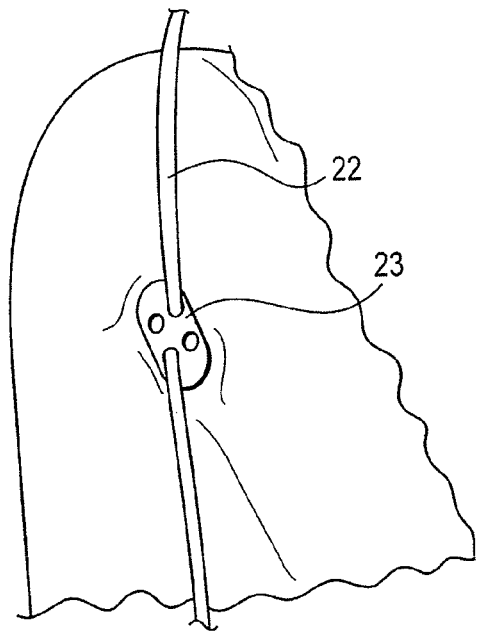
FIG. 19 illustrates the stifle joint of FIG. 8 at a stage subsequent to that shown in FIG. 18 and shows the pulling of the free ends of the suture tape of the construct.

Referring to FIGS. 18-19, all slack in the suture tape 22 is removed by pulling on the suture tape 22 at the tibial hole on the lateral side to ensure that the first button 21 (FIG. 15) is seated firmly. Any remaining slack in the suture tape 22 is removed by pulling on the free ends of the suture tape 22 near the second button 23.

Figure 20:
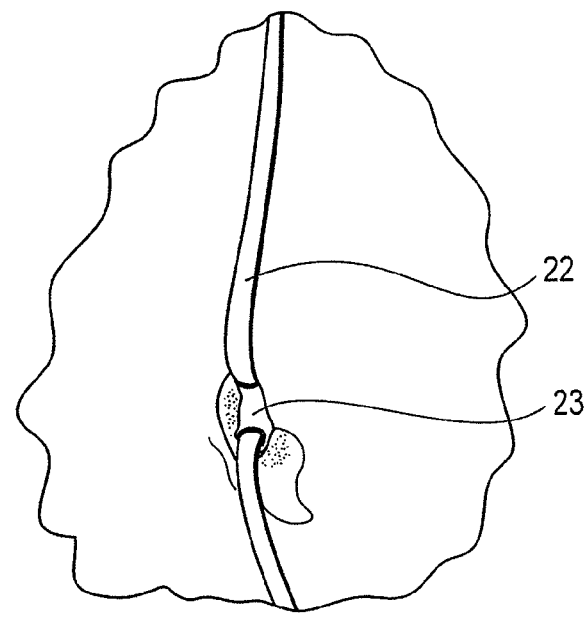
FIG. 20 illustrates the stifle joint of FIG. 8 at a stage subsequent to that shown in FIG. 19 and shows the seating of a button against the femoral bone.
Figure 21:
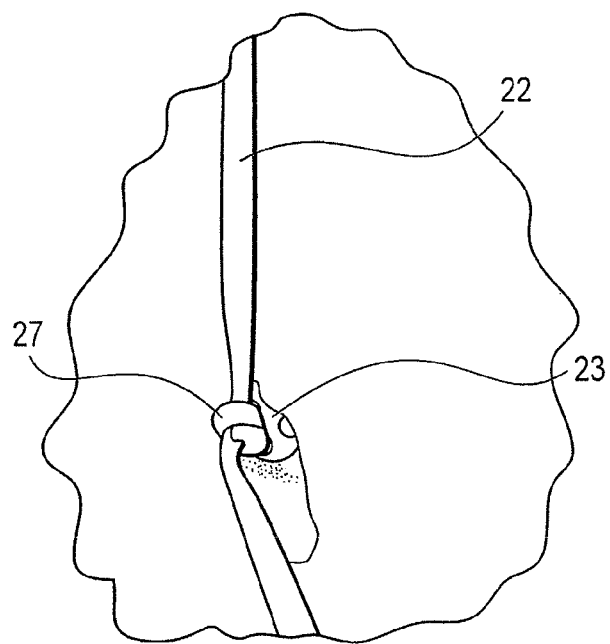
FIG. 21 illustrates the stifle joint of FIG. 8 at a stage subsequent to that shown in FIG. 20 and shows a surgeon's knot.

Subsequently, the second button 23 is advanced through the soft tissue and is seated against the femoral bone, as shown in FIG. 20. The suture tape 22 is pulled to the desired tension on the medial side of the femur. Referring to FIG. 21, a surgeon's knot 27 and two half hitches are tied in the suture tape while holding the stifle joint at a desired angle. The stifle joint is then tested for stability and motion. Two or three additional half hitches are then tied. Any excess suture tape is cut away.

Figure 22:
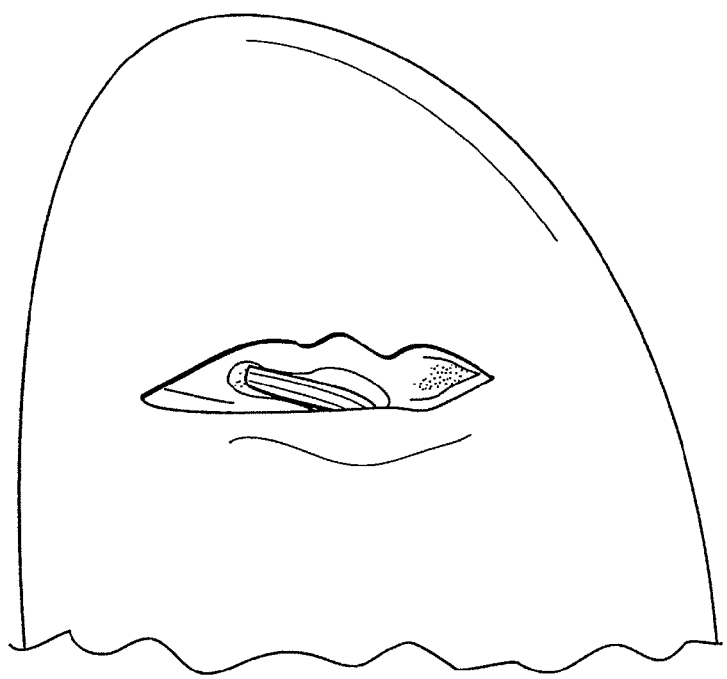
FIG. 22 illustrates the stifle joint of FIG. 8 at a stage subsequent to that shown in FIG. 21 and shows a lateral view of the stifle joint.
Figure 23:
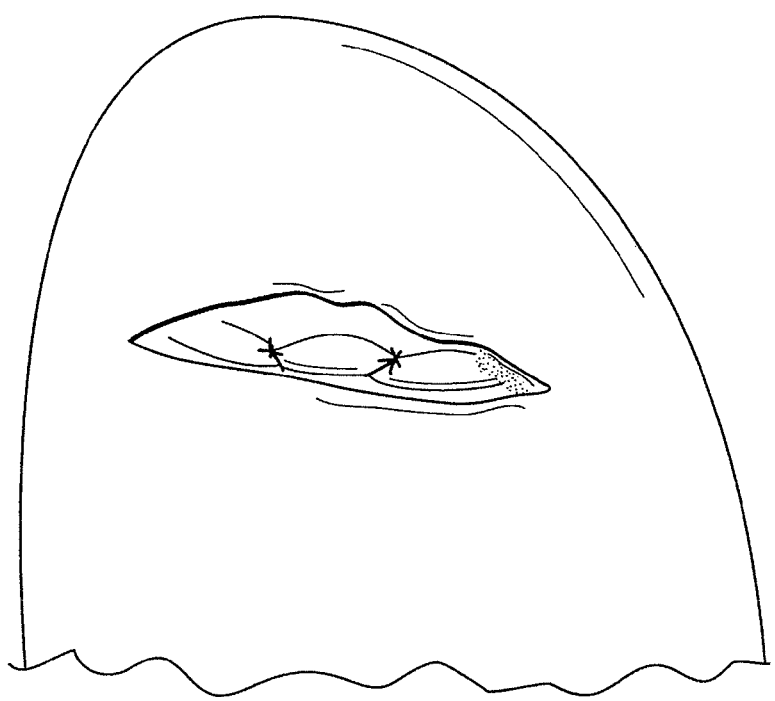
FIG. 23 illustrates the stifle joint of FIG. 8 at a stage subsequent to that shown in FIG. 22 and shows the closing of the muscle and fascia over a button.

Finally, as shown in FIGS. 22-23, the muscle and fascia over the second button and knot are closed in a routine fashion. The lateral fascia is imbricated and the lateral subcutaneous tissues and the skin are closed in a routine fashion.

Implant Removal

Routine removal of the suture-button construct is typically not required. If, for any reason, the buttons need to be removed, this can be performed simply by small incisions over the first and the second button, cutting the suture tape(s) as it loops through the buttons and removing both the first and second buttons and the suture tape(s).

Suture-Button Construct

Second Embodiment

Figure 24:
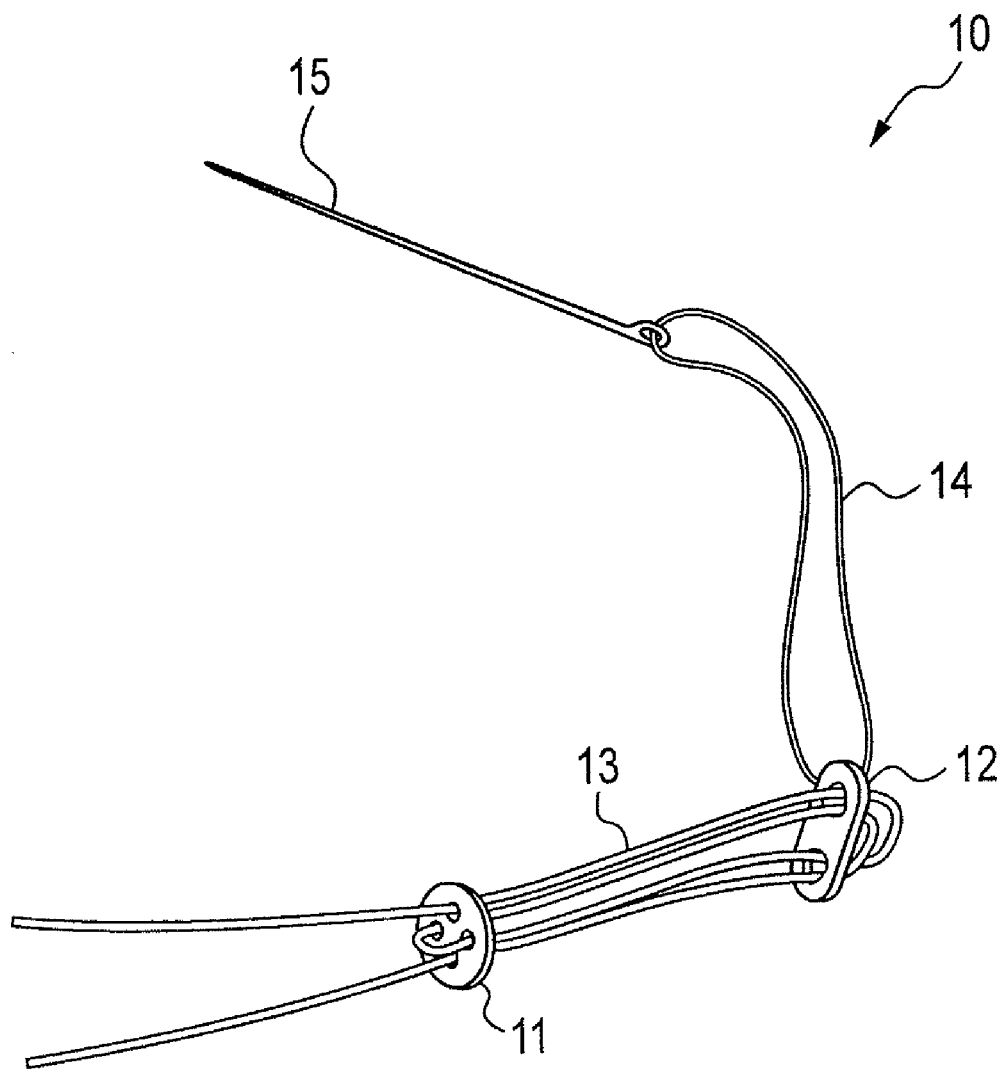
FIG. 24 illustrates a perspective view of assembled suture-button construct, in accordance with a second embodiment of the present invention.
Figure 25B:
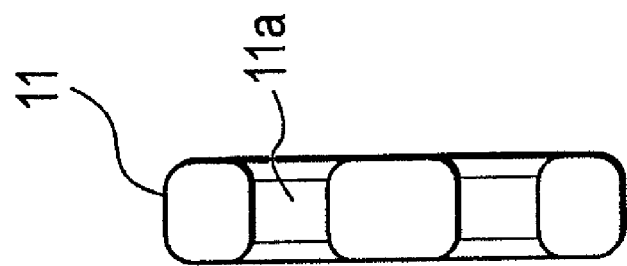
FIG. 25 illustrates a front and side view of a round button which forms part of the suture-button construct, in accordance with the second embodiment of the present invention.
Figure 25A:
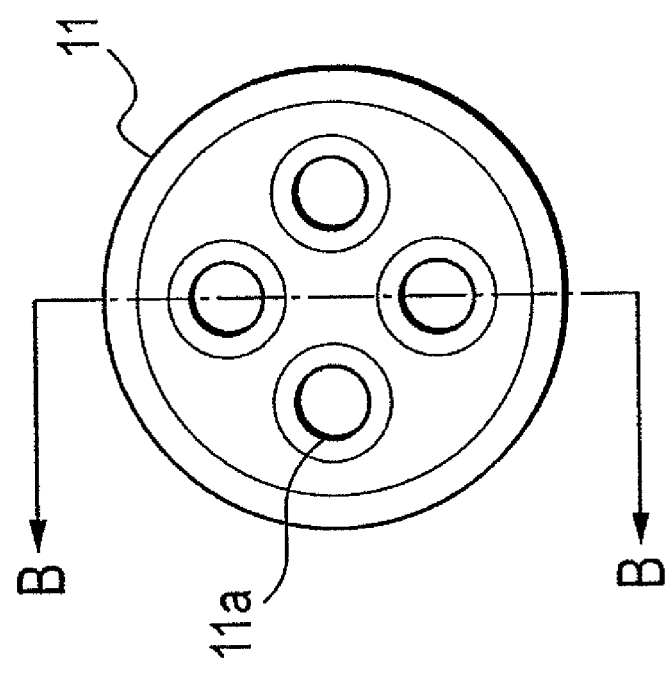
Figure 26B:
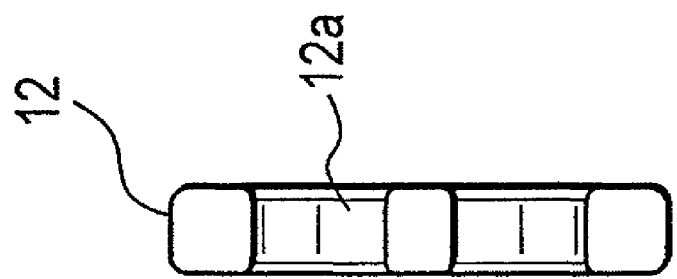
FIG. 26 illustrates a front and side view of an oblong button which forms part of the suture-button construct, in accordance with the second embodiment of the present invention.
Figure 26A:
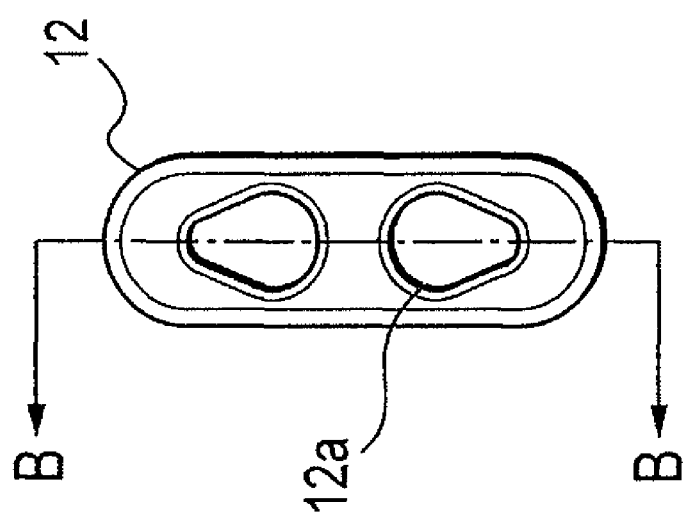

Referring to FIG. 24, a suture-button construct 10, in accordance with a second embodiment of the present invention, is formed of a third button 12, a fourth button 11, a first suture strand 13 double looped through the apertures 11a (FIG. 25), 12a (FIG. 26) of the first button 11 and the second button 12. The suture-button construct 10 also includes a pull-through needle 15 with a pull-through suture strand 14 looped through an aperture 12a (FIG. 26) of the first button 12. The first button 12 is preferably oblong in shape (FIG. 26). The second button 11 is preferably round in shape (FIG. 25).

TABLE 1

| Apparatus of the present invention | |
|---|---|
| First Button | |
| Overall dimensions: | 8.0 mm (length) × 2.6 mm (width) × 1.3 mm (thickness) |
| Basic shape: | Oblong in plan shape, with chamfered or rounded corners and edges - this reduces the chance of the button being palpated under the skin and in addition, eases the passage of the first button through the hole as will be explained hereinafter |
| Button material: | Titanium, stainless steel, PEEK or PLLA |
| Button apertures: | 2 apertures (triangular in plan shape) |
| Aperture dimensions: | 2 mm base × 2 mm perpendicular height (equilateral triangle with chamfered corners), 1 mm distance between first and second apertures |
| Second Button | |
| Overall dimensions: | 5.5 mm (diameter) × 1.27 mm (thickness) |
| Basic shape: | Round in plan shape, with chamfered or rounded corners and edges |
| Button material: | Titanium, stainless steel, PEEK or PLLA |
| Button apertures: | 4 apertures (circular in plan shape), centers of the apertures at about 1.27 mm from the center of the button |
| Aperture dimensions: | 0.95 mm (diameter) (free of burrs or sharp edges) |
| First suture strand | |
| Suture material: | #5 FiberWire ®, blue in color (FiberWire ® is made of ultra-high molecular weight polyethylene (UHMWPE) and polyester, braided over a UHMWPE core) |
| Suture use: | Looped twice through the first and second apertures of the first and second buttons, leaving the two free ends of suture strand free for tying. |
| Pull-through suture strand | |
| Dimensions: | 0.330-0.381 mm (diameter), 0.75 mm (length) |
| Suture material: | #2 FiberWire ®, white in color (FiberWire ® is made of ultra-high molecular weight polyethylene (UHMWPE) and polyester, braided over a UHMWPE core) |
| Suture use: | Looped once through an aperture of the first button, both free ends of pull-through suture strand being attached through the eye of the pull-through needle |
| Suture color: | D&C Blue, White, White/Green |
| Pull-through needle | |
| Dimensions: | 127 mm (length), 1.6 mm (diameter), with pull-through suture strand attached |
| Material: | Stainless steel |
| Eyelet dimensions: | 0.1 mm (length), 0.965 mm (diameter) |

TABLE 1-continued

| Apparatus of the present invention | |
|---|---|
| Guidewire | 1.2 mm (diameter) |
| Cannulated Drill Bit | |
| Dimension: | 178 mm (length) × 2.7 mm (diameter), 1.35 mm cannulation for a guidewire to pass through |
| Material: | Stainless steel |

The first suture strand used in the present invention may be of any material, which is suitable for this purpose, whether absorbable or non-absorbable, monofilament or poly braided, provided it is sufficiently strong. A #2 FiberWire® suture strand may be used. The #2 FiberWire® is a braided suture strand with an ultrahigh molecular weight polyethylene core and has almost twice the strength of a similarly sized generic suture strand. The #2 FiberWire® suture strand is a non-absorbable suture strand with increased abrasion-resistance, which knots easily without slipping. FiberWire® is sold by Arthrex, Inc. of Naples, Fla., and disclosed in U.S. Pat. No. 6,716,234, the disclosure of which is incorporated by reference While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is not to be considered as limited by the foregoing description.

What is claimed is:

1. A method to stabilize a cranial cruciate ligament deficient stifle joint of a canine comprising a lateral fabella, a tubercle of Gerdy, a long digital extensor, a fascia, a distal femur having a femoral condyle and a distal diaphysis, a fascia, and a proximal tibia, the method comprising the steps of:
making an incision from the lateral fabella to the tubercle of Gerdy;
drilling a tunnel through the distal femur of the canine from a location with the caudal portion of the lateral femoral condyle, traversing the distal femur and exiting the distal diaphysis of the femur on the medial side;
palpating the long digital extensor in the extensor groove of the proximal lateral tibia;
making an incision in the fascia caudal to the long digital extensor tendon;
drilling a tunnel through the proximal tibia of the canine from location caudal to the tubercle of Gerdy, traversing through the proximal tibia and exiting the tibia on the medial side;
passing a pull-through needle with attached suture, in a medial to lateral direction, through the tunnel in the femur;
passing the pull-through needle with attached suture, in a lateral to medial direction, through the tunnel drilled in the tibia;
applying sufficient tensile force to ends of the suture passing through the tunnels drilled in the tibia and in the femur to operatively stabilize the cranial cruciate ligament deficient stifle joint;
securing the ends of the suture at respective exit ends of the tunnels drilled in the femur and tibia.

2. The method of claim 1, wherein the ends of the suture are secured with respective buttons.

* * * * *